United States Patent [19]

Bihari et al.

[11] Patent Number: 5,013,739
[45] Date of Patent: May 7, 1991

[54] METHOD OF TREATING CHRONIC FATIGUE SYNDROME USING AN OPIATE RECEPTOR ANTAGONIST

[76] Inventors: Bernard Bihari, 29 W. 15th St., New York, N.Y. 10011; Finvola Drury, 25 Colby St., Rochester, N.Y. 14610

[21] Appl. No.: 433,152

[22] Filed: Nov. 8, 1989

Related U.S. Application Data

[63] Continuation-in-part of Ser. No. 129,862, Dec. 4, 1987, Pat. No. 4,888,346, which is a continuation-in-part of Ser. No. 916,180, Oct. 7, 1986, abandoned.

[51] Int. Cl.$^5$ ............................................. A61K 31/44
[52] U.S. Cl. ................................................... 514/282
[58] Field of Search ........................................ 514/282

[56] References Cited

U.S. PATENT DOCUMENTS

| 4,537,878 | 8/1985 | Plotnikoff | 514/2 |
| 4,857,533 | 8/1989 | Sherman et al. | 514/282 |
| 4,863,928 | 10/1989 | Atkinson | 514/282 |

OTHER PUBLICATIONS

Prieto, J. et al., Naloxone Reversable Monocyte Dysfunction in Patients with Chronic Fatigue Syndrome, Scand *J Immonol* 30(1):13-20 (1989) (Abstract).

*Primary Examiner*—Allen J. Robinson
*Assistant Examiner*—Gary E. Hollinden
*Attorney, Agent, or Firm*—William J. Daniel

[57] ABSTRACT

Chronic herpes viral infections, including chronic genital herpes caused by the herpes simplex virus, Type 2, and chronic infections due to the Epstein-Barr virus, chronic fatigue syndrome, chronic inflammatory connective tissue disease, including rheumatoid arthritis and systemic lupus erythematous and related diseases, and multiple sclerosis are treated by the administration via a pharmacologically effective route of an essentially pure opiate receptor antagonist, preferably an essentially pure opiate receptor antagonist exhibiting a substantially higher blocking effectiveness against Mu opiate receptor sites than against Delta receptor sites, exemplified by naltrexone and naloxone, at a low dose concentration, corresponding to about 1-10 mg per day for naltrexone, at which concentration Delta blocking activity is small, while Mu blocking activity is significant.

5 Claims, No Drawings

![5,013,739]

METHOD OF TREATING CHRONIC FATIGUE SYNDROME USING AN OPIATE RECEPTOR ANTAGONIST

CROSS REFERENCE TO RELATED APPLICATION

This application is a continuation-in-part of copending application Ser. No. 129,862, filed Dec. 4, 1987, now U.S. Pat. No. 4,888,346 issued Dec. 19, 1989, which is a continuation of application Ser. No. 916,180, filed Oct. 7, 1986, now abandoned.

FIELD OF THE INVENTION

This invention relates to the treatment of certain chronic diseases; namely, chronic infections caused by herpes virus, both herpes simplex virus and Epstein-Barr virus, chronic long-term inflammatory disease of the connective tissue, chronic fatigue syndrome and multiple sclerosis, by the low dose administration of an essentially pure opiate receptor antagonist, such as naltrexone and naloxone.

BACKGROUND OF THE INVENTION

In our copending application Ser. No. 129,862, and its parent, identified above, we disclosed and claimed the treatment of humans infected with HTLV-III (AIDS) virus, including clinically diagnosed AIDS and AIDS-related complex (ARC), by the administration at low dosage levels of an essentially pure opiate receptor antagonist, preferably such antagonist having preferential blocking activity for Mu over Delta opiate receptor sites and exhibiting at the contemplated low dosage level a substantially selective blocking activity for Mu over Delta receptor sites, exemplified by naltrexone and naloxone. The patent literature relating to the medical utility proposed at the time for these and related drugs is summarized in the introductory discussion of the earlier application, the complete contents of which are hereby incorporated by reference, and include the treatment of narcotic addiction and narcotic overdose, the relief of severe itching in conjunction with Hodgkin's Disease, mycosis funoides, severe jaundice, and various types of pruritis, the treatment of anorexia, the treatment of medical shock; i.e., anaphylactic, burn, cardiac, and the like shock, and the treatment of alcoholism or alcoholic intoxication.

As explained in the prior applications, essentially pure opiate receptor antagonists, exemplified by naltrexone and naloxone, appear to be effective in potentiating the natural human immune system against the HTLV-III (AIDS) virus, apparently by up-regulation of the endorphinergic system to thereby enhance homostatic regulation of the natural immune function of the human body in ways by no means adequately understood. It has now been discovered that surprisingly these drugs are likewise effective for the treatment of certain chronic long-term diseases for which a specific medical treatment has been largely unavailable up to now, and even their etiology is, in a majority of instances, unknown.

DETAILED DESCRIPTION OF THE INVENTION

The diseases with which the invention is particularly concerned are listed below, together with a summary description of their pertinent medical features.

CHRONIC HERPES VIRUS INFECTIONS

The important herpes virus infections are chronic genital herpes and chronic infections due to the Epstein-Barr virus (EPV). Genital herpes is a highly prevalent disease caused by the herpes simplex virus (HSV) type No. 2, transmitted from person to person by direct contact. The disease typically begins with a genital rash and mild itching which develops into vesicular lesions appearing mainly on the genitalia and adjacent body regions, which leasions can expand to an ulcerated condition, which can be accompanied by a general malaise, fever and anorexia. Neurological complications are possible but rare. The disease is often self-limiting and may disappear after a single episode or, more typically, can reoccur in milder and less frequent episodes; but for some, it can be become chronic with severe and painful episodes at weekly or monthly intervals. Such episodes can be precipitated by stress, trauma, menstrual hormone changes, etc. The chronic disease is usually associated with high levels of serum antibodies against HSV. There is presently no cure for genital herpes. Treatment with the anti-viral drug, acylovir, administered in topical form appears to limit episodic duration but does not effect a cure, prevent transmission or protect against subsequent reoccurrence. Otherwise, treatment is generally palliative. Substantial risk exists for infants delivered by normal birth from infected mothers; neonatal herpes can cause brain damage and possible death.

EBV is the cause of infectious mononucleosis which occurs mainly in late adolescence and young adults by transmission of the virus through direct oral contact. Its symptoms are "flu-like" and mainly include headache, sore throat, muscle soreness, swollen glands, and general fatigue and weakness. These symptoms usually dissipage within a few weeks and treatment consists mainly of rest and curtailed activities combined with analgesic administration to relieve pain and soreness, there being no curative treatment known. Occasionally, the condition becomes recurrent or chronic which is particularly indicated by serological evidence of EBV and a significant increase in lymphocytes, with a large atypical fraction. In chronic cases, the "flu-like" symptoms may persist for a considerable period, and it is this category with which the invention is concerned.

CHRONIC INFLAMMATORY CONNECTIVE TISSUE DISEASE

The most important inflammatory connective tissue diseases are rheumatoid arthritis (RA) and systemic lupus erythematosus (SLE).

RA is an inflammatory disease affecting the connective tissue of the joints and elsewhere in patients of all ages but mainly between 20 and 40. It occurs about equally in both sexes but with a considerably higher likelihood of severity in females. It begins typically in mild form with one or more joints becoming painfully inflamed and stiff accompanied by malaise, fever and weight loss. For some the episodes may be mild and separated by lengthy remissions, but more generally the episodes become more severe and frequent in a continuing pattern of remissions and exacerbations. Its cause is unknown, and opinion is divided over whether it is due to an auto-immune reaction of the body, infection by some unidentified virus or bacteria, or an inherited genetic predisposition. The chronic form can lead to both cartilage destruction and loss of muscle control at the joint. Degenerative effects may also occur in the collagen in various bodily organs. Curative treatment is unknown; treatment is symptomatic and usually involves the administration of anti-inflammatory drugs, most commonly aspirin. The objective is mainly to achieve tolerance and acceptance by the patient with activity aimed at maintaining joint mobility.

Systemic lupus erythematosus is a chronic inflammatory disease of connective tissue throughout the body and usually appears in a pattern of remissions and acute episodes. It occurs primarily in females, mainly of childbearing age, but any age can be affected, being about eight times more prevalent in females than in males The black race is several times more susceptible than the white race. SLE is a syndrome and can affect various organs of the body; it is usually manifested by fever, weight loss, joint pain, skin lesions and rash. Renal, cardiovascular and pulmonary complications are common. Its origin is unknown but apparently is due to an inexplicable defect in the immune system. Contributing factors include exposure to ultraviolet radiation; e.g., from sunlight, infection and hormonal effects. No treatment is known; anti-inflammatories or analgesics are given for symptomatic relief together with corticosteroids and in extreme cases immunosuppressive agents.

MULTIPLE SCLEROSIS

MS is a chronic neurological disease resulting in destruction of the myelin covering of nerve cells, particularly of the brain and spinal cord. It affects men and women equally, mainly between the ages of 20 and 40. Etiological evidence is mixed. Certain evidence suggests an infectious (viral) factor since occurrence is far more common in temperate regions than in tropical regions. Other evidence suggests auto-immune involvement changes in the seriology of the auto-immune system being usually evident prior to acute attacks. Still further evidence suggests a genetic predisposition, persons of Oriental and African ancestry being generally free of the disease independently of origin of birth. Or a combination of all three could be involved in that exposure to a virus at an early age, by which most individuals are unaffected, could after a period of latency trigger in genetically susceptible individuals an auto-immune response. Symptoms of the disease include physical weakness, loss of muscular coordination, unusual burning or prickling sensation and disturbances of speech and vision, especially double vision. Diagnosis is difficult and usually requires a considerable history. For some, the disease may effectively disappear after an attack or two with no disabling consequences. More generally, there is a pattern of relapse and spontaneous remission over time with progressive neurologic disfunction, causing increasing spasticity and loss of coordination. There is no curative treatment for MS; severity of a relapse may be reduced by treatment with corticosteroids, but without apparent long term beneficial effect. Administration of immuno-suppressive agents and interferon have proved ineffective. Treatment is by rest and exercise and aims mainly at diminishing the severity of the physical effects of the disease and adaptive adjustment of the patient's lifestyle.

CHRONIC FATIGUE SYNDROME

CFS has been accepted as a disease only recently and is still subject to considerable uncertainty. It occurs principally in young adults but can appear from childhood through middle age. Symptomatically, its chief characteristic is chronic debilitating fatigue persisting over many months or even years, requiring adaptive changes in lifestyle for coping and in a significant few resulting in total disability. Associated with chronic fatigue in most instances are such symptoms as sore throat, muscle pain, headache, depression, and impairment of concentration and sleep. Diagnostically, the disease is one of "exclusion" as that possibility remaining after elimination of other organic diseases with similar symptoms. Early studies found an association with high levels of antibodies against EBV, but later evidence has questioned the validity of this association, at least in terms of a casual relationship, the EBV antibody level: variations frequently lacking a statistical significance or even being within normal limits in some cases. Evidence of an immunological involvement has been reported such as changes in the "natural Killer" cell population and loss of cytotoxicity against common infectious agents but such changes are also variable to nonexistent.

Recent press reports indicate that the anti-viral agent acyclovir, otherwise effective against EPV, was no more effective than a placebo in treating CFS, thus putting into question the etiological involvement of EBV in this malady.

The distinction between CFS, chronic EBV infection and/or chronic infectious mononucleosis is presently unclear. These conditions may be separate and distinct diseases or they may represent different stages of a single wide-ranging disease. There is no present treatment for CFS other than symptomatic.

Except for chronic fatigue syndrome, the above disease summaries were extracted in simplified and condensed form from *The Encyclopedia and Dictionary of Medicine, Nursing, and Allied Health* by Miller and Keane, W. B. Saunders Co. 3rd Edition, April 1983, and Cecil *Essentials of Medicine* by Andreolin et.al., W. B. Saunders Co., copyright 1986. Information for CFS was taken from the following papers to which reference may be had:

Tosato et.al., Characteristic T Cell Dysfunction in Patients with Chronic Active Epstein-Barr Virus Infection (Chronic Infectious Mononucleosis), *The Journal of Immunology*, Vol 134, No. 5, 3082-3088.

Straus et.al., Persisting Illness and Fatigue in Adults with Evidence of Epstein-Barr Virus Infection, *Annals of Internal Medicine*, Vol. 102, No. 1, 7-16.

Jones et.al., Evidence for Active Epstein-Barr Virus Infection in Patients with Persistent, Unexplained Illnesses: Elevated Anti-Early Antigen Antibodies, *Annals of Internal Medicine*, Vol. 102, No. 1, 1-7.

Caligiuri et.al., Phenotypic and Functional Deficiency of Natural Killer Cells in Patients with Chronic Fatigue Syndrome, *Journal of Immunology*, Vol, 138, No. 10, 3306-3313.

Holmes et.al., A Cluster of Patients with a Chronic Mononucleosis-like Syndrome, *JAMA*, Vol. 257, No. 1, 2297-2302.

Komaroff, The 'Chronic Mononucleosis' Syndromes, *Hospital Practice*, May 30, 1987, 71-75.

Buchwald et.al., Frequency of 'Chronic Active Epstein-Barr Virus Infection' in a General Medical Practice, *JAMA*, Vol. 257, No. 17, 2303-2307

In view of the highly diverse nature of the several diseases with which this invention is concerned, it is quite unexpected that they as a group could be successfully treated by the administration of the essentially pure opiate antagonists of the invention, especially at the extremely low dosage levels herein contemplated. RA, SLE, and MS all share an apparent common association with auto-immune action but for such action, enhancement of the natural immune function of the body, as is believed to be achieved by the invention, would seem to be directly contraindicated. Indeed, as the above discussions indicate, treatment with immunosuppressive agents has been considered as one approach in the management of these diseases. As regards herpes infections, to the extent that a chronic state of infection might indicate an impairment of the immune function of the body, it is nonetheless surprising that the treatment of the invention could induce such a significant improvement in immune function as to actually prove efficacious for these diseases.

The therapeutic agents useful in the present method are the essentially pure opiate antagonists. It is generally accepted that drugs exert their characteristic physiological action in the body by interacting or complexing with certain so-called receptor sites existing in cells in the brain and elsewhere. An opiate antagonist has the capability of interacting with those specific receptor sites which are sensitive to opiate or narcotic drugs, and so long as such interaction persists and of thereby blocking such receptor sites from any additional interaction with the opiate drugs and in this manner preventing the opiate drugs from exerting their characteristic analgesic and euphoric action on the body. These opiate antagonists which do not exert any physiological action of their own are deemed essentially pure and are suitable for purposes of this invention. The great majority of drugs found to possess antagonist action also exert a significant agonist action and are referred to as "mixed agonist/antagonists". Such mixed agonist/antagonists are not suitable for use in the present method which requires essential purity in the antagonist effect.

There appear to be several different kinds of receptor sites that are sensitive to opiates or narcotics, perhaps five or so, and the important sensitivity is possessed by those identified as Mu and Delta receptor sites. The Mu receptor sites have particularly strong affinity for opiate drugs and produce a correspondingly strong physiological (agonist) reaction upon interaction with such drugs. Blockage of the Mu receptor sites is hence an important objective of the invention. Any essentially pure opiate antagonist is effective in blocking Mu receptor sites and thus would be advantageous to at least some extent for achieving the therapeutic results of this invention.

Delta receptor sites, on the other hand, appear to contribute to an effectively functioning immune system when unblocked. It is, therefore, preferred to select an essentially pure opiate antagonist which possesses a preferential blocking action for Mu receptor sites over Delta receptor sites in order to leave the latter in unblocked condition. Such preferential blocking action of Mu sites over Delta sites may be dosage related; that is, a particular antagonist can have an effectively stronger blocking action for Mu sites than for Delta sites at a given dosage range; whereas at higher levels, the amount may be enough to block both sites in substantial entirety. By appropriate selection of the dosage level, one can achieve with a given antagonist, a significant and valuable blocking action against Mu receptor sites while maintaining the blocking action against Delta sites at appreciably lower levels at which the blocking effect on the Delta sites is minor or at least inconsequential. If increasingly higher dosages were to be employed, then ultimately both Mu and Delta sites would both become blocked, which is less advantageous in therapeutic results and preferably to be avoided. However, by judicious adjustment of the dosage level, one can take advantage of the differential between the Mu blocking and Delta blocking capabilities and achieve an effective blocking of Mu sites with only minimal blocking of the Delta sites which is optimum for therapeutic purposes.

Naltrexone and naloxone are both essentially pure opiate antagonists which also exert strong preferential blocking action against Mu over Delta sites, the Mu blocking action being generally rated at about ten times the Delta blocking action. Both of these drugs are presently commercially available and are, so far as is known, the only essentially pure opiate antagonists which have received governmental approval for administration to humans. Both of these drugs can be employed in the practice of this invention with naltrexone being the preferred choice. If other essentially pure opiate antagonists, preferably those exerting significant preferential action against Mu over Delta receptors, become available and receive governmental approval, such drugs, at least in principle, qualify for application in the present method.

The therapeutic agent should obviously be administered by a pharmacological mode or route of administration which is effective for the particular drug. Naltrexone can be administered effectively orally; i.e., in the form of tablets, capsules, caplets, powder, a powdered suspension or solution in a suitable liquid carrier or the like. It is not available in a form suitable for administration by injection. On the other hand, naloxone has not proved to be effective when administered orally at least at dosage levels which would be practical and appropriate in this invention. It is, however, available in forms suitable for administration by injection and can be applied by this mode in the invention if desired. Generally, oral administration is preferable from the standpoint of simplicity and convenience and naltrexone is thus the preferred choice. However, for those patients for whom oral administration is not permissible, administration of naloxone by injection, either intravenously, intramuscularly, or subcutaneously, is an alternative.

The useful dosage range, at which Mu receptor sites are substantially blocked while the Delta sites are substantially unblocked, for naltrexone is about 1-10 mg/day daily. The limits of this range are not critical but below about 1 mg the therapeutic effect is quite small, while at levels several times above 10 mg at which these drugs have been generally administered in the past for other purposes, especially narcotic addiction, the effects of the preferential blocking action against Mu over Delta receptor sites disappears, since the amount of the drug is large enough to cause at least substantial blocking of Delta sites while the Mu sites remain fully blocked. A preferred range for naltrexone is about 1.5-3.0 mg/day daily.

The dosage levels for naloxone and any other essentially pure opiate antagonist that might become available in the future are to be determined with reference to the above-specified dosage ranges for naltrexone. That is, the dosage level for naltrexone or any new essentially pure opiate antagonist should be such as to produce an antagonist effect which corresponds or is equivalent to that produced by naltrexone at the range of about 1-10 mg/day. Such equivalent amounts can be readily determined for other opiate antagonists. Morphine is well recognized as a classical Mu agonist, and other antagonists than naltrexone can be readily standardized against morphine to quantify the amounts thereof that are equivalent to the effective dosage for naltrexone. For example, by means of tests evaluating the response of rats or mice, e.g., the "tail flick" test, that amount of morphine which is offset or counteracted in its narcotic dependency effect by a given amount of naltrexone can then be tested against other antagonists to determine the specific amount of the latter which is necessary to produce the equivalent antagonist action against morphine as the naltrexone. For further information concerning such tests, reference may be had, for example, to the text *Principles of Drug Action: The Basis of Pharmacology*, Goldstein et.al., second edition, copyright 1974, John Wiley & Sons, at pages 604-609 in particular.

EXAMPLES

(1) Genital Herpes

A 50 year old woman has had genital herpes for 13 years, experiencing a severe painful attack with several lesions for the 4-5 days preceding each menstrual period during most of that time. She was started on low dose naltrexone (1.75 mg per day at bedtime). Her attacks immediately stopped. Ten months later the dosage was increased to 2.75 mg/day also taken at bedtime. In the entire period of naltrexone treatment covering a number of months, she has had only two attacks each occurring 2-3 weeks after she ran out of naltrexone and interrupted the treatment temporarily.

(2) Multiple Sclerosis (M.S.)

A. A 26 year old woman had an attack of transverse myelitis several years ago at the lower thoracic level, with a paraparesis involving marked weakness and numbness of both legs. This gradually cleared over a two month period. Four months after the first attack, she had a second episode of transverse myelitis at the cervical level, with symptoms involving her arms and legs, and the diagnosis of multiple sclerosis was made. This gradually cleared. An attack of transverse myelitis at the lower thoracic level occurred four months later, her third attack in eight months. As she was recovering from this attack, she started on naltrexone, 1.75 mg per day at bedtime. Her only subsequent attack in the intervening period of many months occurred one year later, three weeks after she voluntarily discontinued naltrexone. This attack involved weakness and numbness of the left arm. She immediately resumed her low dose naltrexone treatment and has had no attacks since.

B. A 65 year old woman with M.S. of thirty years duration was started on naltrexone. Her M.S. is of the slow deteriorating type with slowly increasing weakness, spasticity and in coordination of her arms and legs with some deterioration apparent to her physicians on each six months follow-up visit. Over a number of months since starting the naltrexone, the disease has stabilized and the progressive deterioration has stopped.

(3) Rheumatoid Arthritis

A 28 year old woman with a positive family history of rheumatoid arthritis has had rheumatoid involvement of her cervical spine, wrist, fingers and knees for five years, unresponsive to a number of nonsteroidal anti-inflammatory agents. She was started on naltrexone, 2.75 mg per day at bedtime several months ago. Over the immediately following two weeks her joint pain and swelling decreased by 75%, most dramatically on the extremities. The improvement has persisted during that time.

(4) Chronic Fatigue Syndrome

A 31 year old woman had suffered from chronic fatigue syndrome for one year with marked fatigue each day beginning in the early or mid afternoon. There has been some accompanying muscle aching, but no symptoms of central neuro system involvement. Her functioning at work and at home have been seriously impaired. EBV titres were quite high. She was started on naltrexone, 3.0 mg per day at bedtime and experienced complete relief of her symptoms after only thirteen days, and this improvement has been sustained thereafter.

What is claimed is:

1. A method of treating humans suffering from chronic fatigue syndrome which comprises the steps of administering by a pharmacologically effective mode to such patient a therapeutically effective dose of an essentially pure opiate receptor antagonist, said dose corresponding to the therapeutic results produced by Naltrexone in the range from about 1.0 mg to about 10.0 mg.

2. A method of treating humans suffering from chronic fatigue syndrome which comprises the steps of administering by a pharmacologically effective mode to such patient an essentially pure opiate receptor antagonist have a selectively higher blocking action against Mu opiate receptors than against Delta receptors in an amount which is effective to exert a substantial opiate receptor blocking action against Mu receptors but insufficient to exert such action against Delta receptors.

3. The method of claim 2, wherein said opiate receptor antagonist is either naltrexone or naloxone.

4. A method of treating humans suffering from chronic fatigue syndrome which comprises the steps of administering by a pharmacologically effective mode to such patient a therapeutically effective dose of an essentially pure opiate receptor antagonist, said dose corresponding to the therapeutic results produced by Naltrexone in the range from about 1.0 mg. to about 10.0 mg. which within said dosage range exerts an opiate receptor blocking action substantially exclusively toward Mu opiate receptors.

5. The method of claim 4, wherein said opiate receptor antagonist is either naltrexone or naloxone.

* * * * *